United States Patent [19]
Petzoldt et al.

[11] Patent Number: 5,539,111
[45] Date of Patent: Jul. 23, 1996

[54] PROCESS FOR RESOLUTION OF RACEMATES OF 4-ARYL-2-OXO-PYRROLIDINE-3-CARBOXYLIC ACID ESTERS

[75] Inventors: Karl Petzoldt; Ralph Schmiechen; Kurt Hamp; Matthias Gottwald, all of Berlin, Germany

[73] Assignee: Schering Aktiengesellschaft, Berlin, Germany

[21] Appl. No.: 19,534

[22] Filed: Feb. 18, 1993

Related U.S. Application Data

[63] Continuation of Ser. No. 903,117, Jun. 23, 1992, abandoned, which is a continuation of Ser. No. 544,529, Jun. 28, 1990, abandoned.

[30] Foreign Application Priority Data

Jun. 30, 1989 [DE] Germany ............ 39 21 593.8

[51] Int. Cl.⁶ .................. C07D 207/12; C12P 17/10; C12P 17/12; C12P 17/16
[52] U.S. Cl. .................. 544/141; 544/372; 546/208; 548/531; 548/551; 435/117; 435/118; 435/121; 435/122; 435/280
[58] Field of Search .................. 544/141, 372; 546/208; 548/531, 551; 435/117, 118, 121, 122, 280

[56] References Cited

U.S. PATENT DOCUMENTS

| | | | |
|---|---|---|---|
| 4,012,495 | 3/1977 | Schmiechen et al. | 544/82 |
| 4,588,694 | 5/1986 | Hamaguchi et al. | 548/229 |
| 4,732,853 | 3/1988 | Whitesides et al. | 435/280 |
| 4,879,421 | 11/1989 | Kazlauskas | 568/737 |
| 5,180,671 | 1/1993 | Nishizawa et al. | 435/280 |
| 5,286,650 | 2/1994 | Bänziger et al. | 435/280 |

FOREIGN PATENT DOCUMENTS

| | | |
|---|---|---|
| 008645 | 3/1980 | European Pat. Off. |
| 197474 | 10/1986 | European Pat. Off. |

OTHER PUBLICATIONS

Sakimae et al, *Chemical Abstracts*, vol. 112, No. 97019 (1990) (Abstract for JP 63/198998, Aug. 17, 1988).
Francalanci et al, *Chemical Abstracts*, vol. 108, No. 166108 (1988) (Abstract for EP 237983, Sep. 23, 1987).
Iriuchijima et al, *Chemical Abstracts*, vol. 97, No. 106411 (1982).
Iriuchijima et al, *Agric. Biol. Chem.* 46, p. 1593 (1982).
Marivet et al, *J. Med. Chem.*, 32, p. 1450 (1989).
Gu et al, *Tetrahedron Letters* 27 pp. 5203–5206 (1986).

*Primary Examiner*—Emily Bernhardt
*Attorney, Agent, or Firm*—Millen, White, Zelano & Branigan

[57] ABSTRACT

An enzymatic process employing pancreatin or choelsterol esterase for resolution of racemates of 4-aryl-2-oxo-pyrrolidine-3-carboxylic acid esters of general formula I

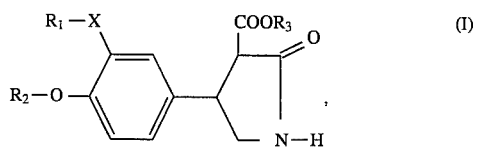

in which X represents a carbon-carbon bond or an oxygen atom, $R_1$ means a hydrocarbon radical optionally substituted by hydroxy groups, oxo groups and/or halogen atoms and/or interrupted by nitrogen atoms with at most 16 carbon atoms, $R_2$ symbolizes an alkyl group with up to 4 carbon atoms and $R_3$ represents an alkyl group with at most 6 carbon atoms is described.

6 Claims, No Drawings

PROCESS FOR RESOLUTION OF RACEMATES OF 4-ARYL-2-OXO-PYRROLIDINE-3-CARBOXYLIC ACID ESTERS

This application is a continuation of application Ser. No. 07/903,117, filed Jun. 23, 1992, now abandoned which in turn is a continuation of application Ser. No. 07/544,529, filed Jun. 28, 1990 now abandoned.

SUMMARY OF THE INVENTION

The invention relates to a process for resolution of racemates of 4-aryl-2-oxo-pyrrolidine-3-carboxylic acid esters of general formula I

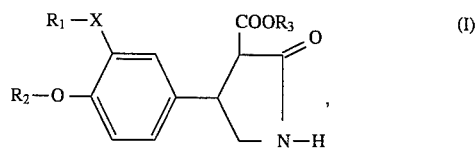

in which

X represents a carbon-carbon bond or an oxygen atom, $R_1$ means a hydrocarbon radical optionally substituted by hydroxy groups, oxo groups and/or halogen atoms and/or interrupted by nitrogen atoms with at most 16 carbon atoms, $R_2$ symbolizes an alkyl group with up to 4 carbon atoms and $R_3$ represents an alkyl group with at most 6 carbon atoms, characterized in that the racemic 4-aryl-2-oxo-pyrrolidine-3-carboxylic acid esters are reacted in aqueous phase with pancreatin or a cholesterol esterase and the formed optically active 4-aryl-2-oxo-pyrrolidine-3-carboxylic acid of general formula II

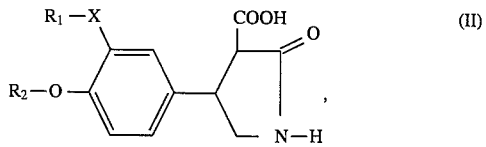

in which X, $R_1$ and $R_2$ have the above-named meaning and/or the unconverted optically active 4-aryl-2-oxo-pyrrolidine-3-carboxylic acid ester of general formula I is isolated in a way known in the art.

The invention further relates to use of the optically active 4-aryl-2-oxo-pyrrolidine-3-carboxylic acids of general formula II and/or optically active 4-aryl-2-oxo-pyrrolidine-3-carboxylic acid esters of general formula I for the production of optically active 4-aryl-2-oxo-pyrrolidines of general formula III

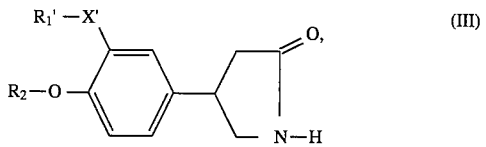

in which $R_1'X'$ has the same meaning as $R_1X$ or represents a hydroxy group and $R_2$ symbolizes an alkyl group with up to 4 carbon atoms.

As is known, 4-Aryl-2-pyrrolidones of general formula III are pharmacologically effective substances. Thus, for example, 4-aryl-2-pyrrolidones of general formula III with $R_1'$ meaning a hydrocarbon with up to 18 carbon atoms or a substituted alkyl group with up to 5 carbon atoms and X' meaning an oxygen atom are described in U.S. Pat. No. 4,012,495, which are suitable for treatment of neurological and mental illnesses. It is stated in WO 86/02268 that these substances are suitable for topical treatment of inflammations.

4-Aryl-2-pyrrolidones of general formula III with $R'_1$ meaning an alkyl group or hydroxy alkyl group substituted by N-heterocycles and X meaning oxygen are described in EP-B 0008645, equivalent to U.S. Pat. No. 4,219,551. These substances are marked by a vasodilative and antihypertensive action.

Further, DE-A 38 23 299 relates to 4-aryl-2-pyrrolidones of general formula III with $R_1$ meaning an aromatic, non-aromatic or heterocyclic ring system and X' meaning a carbon-carbon bond. These substances can be used as active ingredients for psychopharmaceutical agents.

Included among the 4-aryl-2-pyrrolidones of general formula III, 4-[3-cyclopentyl-4-methoxyphenyl]-2-pyrrolidone (=Rolipram) has been thoroughly studied. By a very expensive process, not reproducible on an industrial scale, this compound was converted into its enantiomers and it was established that the (−)-4-[3-cyclopentyl-4-methoxyphenyl]-2-pyrrolidone is the actual pharmacologically effective component, while the corresponding (+)- enantiomer shows only slight effectiveness. Further, with other 4-aryl- 2-pyrrolidones studied the (−) enantiomer pharmacologically is substantially stronger than the (+) enantiomer.

Since it is desirable that with racemic pharmaceutical active ingredients in each case only the effective enantiomer is used for the production of pharmaceutical preparations, an object of the invention was to develop an industrially feasible process for the production of optically active 4-aryl-2-pyrrolidones of general formula III, said process being without substantial problems on an industrial scale. This object was achieved by making the process according to the invention available.

The 4-aryl-2-oxo-pyrrolidine-3-carboxylic acid esters of general formula I serving as initial materials for the process according to the invention can have as the substituent $R_1$ a hydrocarbon radical optionally substituted by hydroxy groups, oxo groups and/or halogen atoms and/or interrupted by nitrogen atoms with at most 16 carbon atoms. Such hydrocarbon radicals are, for example, straight-chain or branched alkyl groups, alkenyl groups or alkinyl groups with at most 8 carbon atoms, cycloalkyl groups with 3 to 6 carbon atoms, cycloalkylalkyl groups with at most 8 carbon atoms, phenyl groups or benzyl groups. These hydrocarbon radicals can be unsubstituted or carry the above-named substituents. As hydrocarbon radicals interrupted by oxygen atoms there can be mentioned, for example, alkoxyalkyl groups with at most 8 carbon atoms, alkoxyphenyl groups and alkoxybenzyl groups with at most 4 carbon atoms in the alkoxy radical or the tetrahydrofuranyl group. As hydrocarbon radicals interrupted by nitrogen atoms there can be mentioned, for example, alkyl groups with 2 to 4 carbon atoms substituted by piperidine, morpholine or piperazine, and the heterocycle, for its part, can be substituted by phenyl groups, benzyl groups or also pyridyl groups. Also these hydrocarbon radicals, interrupted by oxygen atoms and/or nitrogen atoms, can be unsubstituted or be substituted by oxygen atoms, oxo groups and/or halogen atoms (preferably fluorine or chlorine atoms).

Especially preferred initial materials are by nature those 4-aryl-2-oxo-pyrrolidine-3-carboxylic acid esters of general formula I that lead to highly active compounds of general formula III.

Such 4-aryl-2-oxo-pyrrolidones of general formula III are, for example, compounds with X being an oxygen atom, $R_1$ being a saturated or unsaturated, aliphatic or cyclic carbon radical with at most 8 carbon atoms (such as, for example, ethyl, isopropyl, 2-propinyl, cyclopropylmethyl, cyclopentyl or benzyl) $R_2$ being an alkyl group with up to 4 carbon atoms, especially a methyl group, or
compounds with X being an oxygen atom, $R_1$ being the grouping

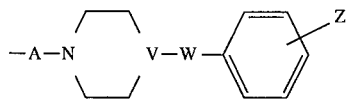

in which

A is an alkylene radical with 2 to 4 carbon atoms substituted by a hydroxy group, V is a nitrogen atom or a methine group, W is an N—C bond, a C—C bond, a methylene group or a carbonyl group and Z is a hydrogen atom or a halogen atom, as well as $R_2$ being an alkyl group with up to 4 carbon atoms, especially a methyl group, or compounds with X being a carbon-carbon bond $R_1$ being a phenyl radical or cycloalkyl radical with 3 to 6 carbon atoms optionally substituted by 1 or 2 halogen atoms as well as $R_2$ being an alkyl group with up to 4 carbon atoms, especially a methyl group.

Preferred initial materials are, on the other hand, also those that contain easily clearable groups R—X— (such as, for example, the benzyloxy group). There can be produced from these substances in a simple way optically active 4-aryl-2-pyrrolidones of general formula III with R'X' meaning an OH group, which, for their part, can be converted by the known processes (U.S. Pat. No. 4,012,495; EP-B 0008645 and DE-A 3823 299) into optically active pharmacologically effective 4-aryl-2-pyrrolidones.

The 4-aryl-2-oxo-pyrrolidine-3-carboxylic acid esters of general formula I used as initial materials can contain as $R_3$ an alkyl group with at most 6 carbon atoms (preferably a methyl group or an ethyl group). They are known, or can be produced from known starting products by the methods described in U.S. Pat. No. 4,012,495.

The racemic 4-aryl-2-oxo-pyrrolidine-3-carboxylic acid esters of general formula I are reacted according to one embodiment of the invention in aqueous phase with pancreatin or cholesterol esterase. For this purpose, the pancreatin or cholesterol esterase is suitably dissolved in aqueous buffer solution of pH 6 to 10, mixed with a solution of the substrate in one of the solvents usually used, such as dimethyl sulfoxide or dimethylformamide, and stirred at a reaction temperature of 10° to 40° C., preferably of 20°–25° C., until about 50% of the substrate has reacted. The substrate concentration usually is 1 to 20 g—preferably 1 to 5 g—per liter of fermentation volume. Since pancreatin has a different composition depending on origin, the necessary amount of pancreatin must be determined by preliminary tests, which are familiar to one skilled in the art. For example, racemic separation of carboxylic acid esters is disclosed in Sh. Iriuchijima et al. (Agr. Biol. Chem. 46:1593–1597, 1982). Here, stereospecific saponification of rac. 1-acetoxy-2,3-dichloropropane to (+)-1-hydroxy-2,3-dichloropropane is performed with pancreatin. (However, this substrate is entirely different from the substrates of the present application.)

In the reaction with pancreatin, preferably up to ten times as much enzyme as substrate is utilized in the present invention. The substrate concentration is preferably 1–5 g/l. The exact conditions must be determined by preliminary tests. With the same substrate concentration, 1–50 mg/l of cholesterinesterase is preferably employed, corresponding to 35–1750 units/l. Here, too, the exact conditions must be found by preliminary experiments.

In the experiments conducted, so far pancreatin preparation and cholesterol esterases, which were obtained from porcine pancreas, have been used almost exclusively, but enzyme preparations of other origins are suitable. An experiment was conducted with cholesterol esterase of bacterial origin; this enzyme proved to be less preferable.

The following enzyme preparations, for example, are preferred for performing the process according to the invention:

Pancreatin pellets "Standard" of Biochemie GmbH AT-Kundl; Product No. 461 173

Pancreatin powder of Merck u. Co., DE-Darmstadt, Product No. 7133

Cholesterol esterase of Fluka Chemie AG, CH-Buchs, Product No. 26746

Cholesterol esterase of Biozyme Lab. Ltd., BG-Bleavanon, Code CE-2 and

Cholesterol Esterase of Chemical Dynamics Corp., US, Plainfield, (N.J.), Product No. 22-2840-00.

If the process according to the invention is performed with the use of cholesterol esterases, it is advisable to add to the reaction mixture a nonionic surfactant such as, for example, an alkyl phenol ethoxylate to stabilize the enzyme, e.g., "Triton" X-100. The use of cholesterol esterases has the advantage that it can be used in substantially smaller concentrations than pancreatin. Moreover, this enzyme has the advantage that it can be used very well for the production of immobilizates.

The immobilization of the enzyme takes place by embedding into a polymer not denaturing this enzyme according to methods which are well known to one skilled in the art (I. Chibata Immobilized Enzymes: Research and Development 1978; S. P. Colowick and N. O. Kaplan, Methods in Enzymology, Academic Press, New York, et al., Vol. 44, 1976 and Bo Matthiasson Immobilized Cells and Organells, CRC Press Inc., Boca Raton, Fla., Vol. 1 and 2).

Thus, for example, cholesterol esterase can be fixed on activated CH-Sepharose® of Pharmacia Fine Chemicals, SE-Upsala or on acrylic resin beads Eupergit® of Roehm Pharma GmbH, DE-Darmstadt. Such an immobilizate, in which 100 mg of cholesterol esterase is bound on 1 g of Eupergit®, according to our own investigations can be used in at least 20 cycles without suffering a significant loss of activity. After the reaction is completed, the immobilizate can be recovered by filtration or centrifuging.

The reaction course can be followed by the usual analytic techniques.

A suitable method is, for example, analysis by thin-layer chromatography or high-pressure liquid chromatography.

After the completed reaction, the optically active 4-aryl-2-oxo-pyrrolidine-3-carboxylic acid of general formula II and the optically active 4-aryl-2-oxo-pyrrolidine-3-carboxylic acid esters of general formula I easily can be separated from one another. This can happen, for example, by the acid being bound on basic ion exchangers or the ester being extracted from the neutral reaction mixture by typical solvents such as ethyl acetate, methyl isobutyl ketone or chloroform, then the reaction mixture is acidified and the free acid extracted. Ester and acid can then be converted by the methods, which are described in U.S. Pat. No. 4,012,495, into optically active 4-aryl-2-pyrrolidones of general formula III.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 21 593.8, filed Jun. 30, 1989, are hereby incorporated by reference.

A. Examples relating to the process according to the invention.

EXAMPLE 1

20 liters of phosphate buffer pH 7, produced by dissolving 145.24 g of disodium hydrogen phosphate dihydrate and 70.4 g of potassium dihydrogen phosphate in 20 l of water, is sterilized for 40 minutes at 121° C. in a steel fermenter holding 30 liters. Then the buffer solution is cooled to 23° C. 200 g of "Pankreatin Granulat Standard" of the Biochemie Gesellschaft m.b.H. Kundl/Tyrol/Austria, Material No. 00461173 is weighed in, in a 2-liter Erlenmeyer flask, briefly stirred with a spatula with 1.5 l of buffer solution taken from the fermenter and immediately transferred into the stirred fermenter (100 rpm). Then it is stirred for 1 minute more and then the substrate, a solution of 40 g of 4-(3'-cyclopentyloxy-4'-methoxy-phenyl)- 2-oxo-pyrrolidine-3-carboxylic acid methyl ester in 400 ml of dimethyl sulfoxide, is added. After that, with the temperature of 23° C. remaining constant, the stirring rate is increased to 220 rpm. After 2 hours stirring under said conditions, 50% of the carboxylic acid ester used has saponified. (The reaction can be followed by thin-layer chromatography on silica gel RP chiral plates of Macherey-Nagel Co./DE 5610-Dueren by toluene-ethyl acetate-glacial acetic acid 70:15:15.)

Now the batch is worked up by the reaction mixture being extracted with an organic solvent in two stages, and the resulting (+) acid and the unsaponified (−) ester are separated from one another.

I. The neutral reaction mixture is first extracted twice with 20 l of methyl isobutyl ketone, the extracts combined and evaporated to dryness in a vacuum. The remaining residue is slowly crystallized by:

23.6 g of (−)-4-(3'-cyclopentyloxy-4'-methoxy-phenyl)-2-oxo-pyrrolidine-3-carboxylic acid methyl ester as cryst. crude product (according to HPLC analysis 76.5%, the yield is calculated from it at 44.4% VE). A sample was chromatographed on a silica gel column and after that recrystallized from methyl isobutyl ketone, then from ethyl acetate:

Melting point 112°–113° C., $[\alpha]_D$ −114.1° (c=1 in methanol)

II. The extracted aqueous reaction mixture is then adjusted to pH 3 with semiconcentrated hydrochloric acid and after that clarified by filtration on a Celite layer. The filtrate is now extracted twice with 20 l each of methyl isobutyl ketone, the extracts are combined and evaporated to dryness in a vacuum. In this case there remains:

21.2 g of (+)-4-(3'-cyclopentyloxy-4'-methoxy-phenyl)-2-oxo-pyrrolidine-3-carboxylic acid as brownish oil (according to HPLC analysis 80.0%, from it the yield is calculated at 44.5% of theory).

A sample was chromatographed on a silica gel column and then crystallized from methanol:

Melting point about 190° C. (not specific), $[\alpha]_D$ +93.4° (c=1 in methanol)

EXAMPLE 2

20 l of phosphate buffer pH 7 is sterilized for 40 minutes at 121° C. in a 30-l steel fermenter and after that thermostated to 23° C.

200 g of pancreatin powder of the Merck company, Darmstadt, article no. 7133, is weighed in, in a 2-l Erlenmeyer flask, stirred with a spatula with 1.5 l of buffer solution taken from the fermenter and immediately transferred into the stirred fermenter (100 rpm). After that it is stirred for one more minute and then the substrate, a solution of 20 g of 4-(3'-benzyloxy-4'-methoxy-phenyl- 2-oxo-pyrrolidine-3-carboxylic acid ethyl ester in 200 ml of dimethyl sulfoxide, is added. Then with the temperature of 23° C. remaining constant, the stirring speed is increased to 220 rpm. After 2 hours of stirring, 50% of the pyrrolidine carboxylic acid ethyl ester used has saponified.

The batch is now worked up, by the reaction mixture being extracted in two stages, by which the resulting (+)-pyrrolidine carboxylic acid is separated from the unsaponified (−)-pyrrolidine carboxylic acid ethyl ester.

I. The (neutral) reaction mixture is extracted twice with 2 ml each of methyl isobutyl ketone, the extracts are combined and evaporated to dryness in a vacuum. 17.2 g of an oily crystalline residue remains.

For purification, the residue is dissolved in 100 ml of ethyl acetate, mixed with 2 g of activated carbon and stirred for 30 minutes at 50° C. After cooling to room temperature, the mixture is filtered through a double plaited filter and the filtrate evaporated to dryness in a vacuum. The residue is taken up in 100 ml of methyl isobutyl ketone and stored overnight in the deep-freezer for crystallization:

$K_1$=9.4 g of (−)-4-(3-benzyloxy-4'-methoxy-phenyl)-2-oxo-pyrrolidine- 3-carboxylic acid ethyl ester as white crystallizate.

A sample was recrystallized twice from ethyl acetate: melting point 90°–92° C., $[\alpha]_D$ −87.0° (c=1 in methanol)

II. The extracted reaction mixture is then acidified with semiconcentrated hydrochloric acid to pH 3 and after that filtered on Celite. The filtrate is now also extracted twice with 20 l each of methyl isobutyl ketone, the extracts are combined and evaporated to dryness in a vacuum. In this case 13.4 g of oily crystalline residue remains.

For purification, the residue is dissolved in 100 ml of in sodium hydroxide solution at 50° C. with stirring, cooled to room temperature and after that extracted 3 times with 50 ml each of ethyl acetate. The organic phases are discarded. The aqueous phase is slowly brought to pH 3 by semiconcentrated hydrochloric acid with stirring, and pyrrolidine carboxylic acid precipitates. It is stirred for 30 minutes more, the precipitate is suctioned off, then dissolved in ethyl acetate, dried with sodium sulfate, filtered and stored overnight in the deep-freezer for crystallization:

$K_1$=6.4 g (+)-4-(3'-benzyloxy-4'-methoxy-phenyl)-2-oxo-pyrrolidine- 3 carboxylic acid as white crystallizate.

A sample is recrystallized one more time from ethyl acetate.

Melting point 145°–146° C., $[\alpha]_D$ +105.2° (c=1 in methanol)

The initial compounds necessary for the enzymatic reactions described in examples 1 and 2 are produced according to the general reaction description illustrated with examples in U.S. Pat. No. 4,012,495. Yields (% of theory) and material data (melting point, crystallization solvent) are summarized in table 1.

TABLE 1

| | R' = —O-cyclopentyl, R = —CH₃ | R' = —OCH₂—C₆H₅, R = —C₂H₅ |
|---|---|---|
| CH₃O—C₆H₃(R')—CHO | Slow crys. oil | Commercial product 64° |
| CH₃O—C₆H₃(R')—CH=C(CO₂R)₂ | 69% Oil | 86% 84° (Ethanol) |
| CH₃O—C₆H₃(R')—CH=CH—CH(CO₂R)(CH₂NO₂) | 97% 96–98° (Diisopropylether) | 91% 80–82° (Ethanol/Diisopropylether) |
| CH₃O—C₆H₃(R')—pyrrolidone-3-CO₂R | 89% 145–148° (Methanol) | 87% 92–93° (Ethanol/Diisopropylether) |

B. Examples relating to the use of products of the process:

The pyrrolidone-3-carboxylic acids or 3-carboxylic acid esters, obtained according to examples 1 and 2, analogously to the way described in U.S. Pat. No. 4,012,495 for the racemates are converted by decarboxylation or saponification and decarboxylation into the enantiomers of 4-(4'-methoxy-phenyl)- 2-pyrrolidone (+)-I or (−)-I (for data see table 2).

The enantiomers of 4-(3'-benzyloxy-4'-methoxy-phenyl)- 2- pyrrolidone (according to example 2) can be converted in a simple way by hydrogenolytic cleavage of the benzyl group into the corresponding 3'-hydroxy compounds.

8.9 g of (+)- or (−)-4-(3'-benzyloxy-4'-methoxy-phenyl)- 2- pyrrolidone is dissolved in 100 ml of ethanol and after addition of 0.5 g of palladium carbon (10%) is hydrogenated with shaking at room temperature and normal pressure until stopping of the hydrogen absorption. After filtering off, it is concentrated by evaporation in a vacuum and the residue is recrystallized (data of 4-(3'-hydroxy- 4'-methoxy-phenyl)- 2-pyrrolidone see table 3, no. 1).

From the 3-hydroxy compounds thus produced, in a known way there can be synthesized by alkylation the enantiomorphic 4-(3'-alkoxy-4'-methoxy-phenyl)-2-pyrrolidone U.S. Pat. No. 4,012,495, EP-A 0008645) or in palladium catalyzed reaction of trifluoromethylsulfonates the enantiomorphic 4-(3'-cycloalkyl or 3'aryl-4'-methoxy-phenyl)- 2-pyrrolidones (DE-P 38 23 299.5. Some representative examples are given in table 3.

TABLE 2

CH₃O—C₆H₃(R')—4-(pyrrolidone-2) (+)-I/(−)-I

| R' | Yield % of th. (+/−) | Crystallization solvent | Melting point (+/−) | $(\alpha)_D^{20}$ c = 1, Methanol (+/−) |
|---|---|---|---|---|
| —O-cyclopentyl | 61,8/71.0 | Ethyl acetate | 133°/133° | +33.8°/−33.0° |
| —OCH₂—C₆H₅ | 65,0/70.0 | Ethyl acetate/ Diisopropylether | 137°/137° | +30.1/−29.7° |

TABLE 3

$$\text{CH}_3\text{O}-\underset{R'}{\overset{}{\text{C}_6\text{H}_3}}-\text{CH}(\text{CH}_2-\text{CO})-\text{NH}$$

| R'— | Yield % of th. (+/−) | Cyrstallization solvent | Melting Point (+/−) | $(\alpha)_D^{20}$ (+/−) | c, solvent |
|---|---|---|---|---|---|
| —OH | 92,0/90,7 | Methanol | 157–158°/157–158° | +35,9°/−35,8° | c = 1; Pyridine |
| —OCH₃ | 67/77 | Ethyl acetate | 133°/133° | +37,9°/−37,6° | c = 1; Methanol |
| —OCH₂C≡CH | 77/82 | Ethanol - Diisopropyl-ether | 116°/116° | +30,9°/−31,4° | c = 1; Methanol |
| —O—(CH₂)₃—N(piperidine)—CO—C₆H₄—F | 53,5/51,0 | Ethanol | 197–198°/197–198° | +19,5°/−18,5° | c = 0,5; Methanol |
| cyclopentyl | 40/43 | Ethyl acetate | 111°/112° | +34,1°/−34,4° | c = 0,5; Ethanol |

*above R' = —OSO₂CF₃

EXAMPLE 3

5 l of phosphate buffer pH 7, produced by dissolving 36.31 g of Na₂HPO₄2H₂O and 17.6 g of KH₂PO₂ in completely softened water, with addition of 15 Triton X-100 (an octyphenolethoxylate of Fluka Chemie AG, CH-Buchs) (0.3%, v/v) is sterilized for 45 minutes at 121° C. in a 10-liter glass fermenter. After cooling of the solution to 23° C., 100 ml of buffer solution is removed, in the latter 50 mg of cholesterol esterase from porcine pancreas of Biozyme Laboratories Ltd., Bleanavon, South Wales, Great Britain, Code CE-2 is suspended, the suspension is again transferred into the fermenter and the reaction mixture is stirred at 220 rpm. The addition of the substrate, of a solution of 10 g of 4-(3'-cyclopentyloxy-4'-methoxy-phenyl)-2-oxo-pyrrdoline- 3-carboxylic acid methyl ester (Rolipram-3-carboxylic acid methyl ester) in 100 ml of dimethyl sulfoxide then immediately takes place. After 72 hours of stirring at 23° C., 50% of the substrate used has saponified.

The batch is worked up by the reaction mixture being extracted in two stages with an organic solvent, and the resulting (+)-Rolipramic acid and the unsaponified (−)-Rolipram ester are separated from one another.

The (neutral) reaction mixture is first extracted twice with 5 l each of methyl isobutyl ketone, the extracts are combined and evaporated to dryness in a vacuum. To remove the coextracted Triton X-100, the residue is mixed with about 400 ml of tap water, stirred for 10 minutes at 50° C., cooled overnight to 20° C. and then suctioned off. There remains a crystalline crude product of 3.8 g of (−)-4-(3'-cyclopentyloxy- 4'-methoxy-phenyl)-oxo-pyrrolidine-3-carboxylic acid methyl ester (according to HPLC 95%, from it a yield is calculated at 36% V.E.). The crude product, analogously to the way described in U.S. Pat. No. 4,012,495 for the racemates, is converted directly into the (−)-4-( 4'-methoxy-phenyl)-2-pyrrolidone by saponification and decarboxylation. The crude product thus resulting without further purification shows, with chromatography in 96% ethanol in microcrystalline cellulose triacetate, a purity of over 98% of enantiomer excess.

The extracted aqueous reaction mixture is then adjusted to pH 3 with half-concentrated hydrochloric acid and also extracted twice with 5 l each of methyl isobutyl ketone, the extracts are combined and evaporated to dryness in a vacuum. There remains a crude product of 7.12 g of (+)-4-)3'-cyclopentyloxy- 4'-methoxy-phenyl)-2-oxo-pyrrolidine-3-carboxylic acid as brownish oil (according to HPLC 73.1%, from it a yield is calculated at 55% of theory), which is converted directly by decarboxylation into the (+)-4-)4'-methoxy-phenyl)- 2-pyrrolidone. The crude product thus resulting has according to chromatography on cellulose triacetate a purity of 92% of enantiomer excess.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the resolution of racemates of 4-aryl-2-oxo-pyrrolidine-3-carboxylic acid esters of the formula I

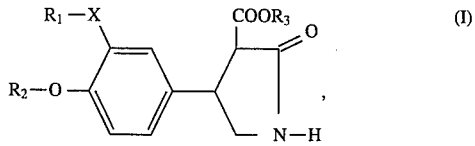

wherein

X is a carbon-carbon bond or an oxygen atom, $R_1$ is a $C_{1-16}$-hydrocarbon radical optionally substituted by at least one hydroxy group, and/or halogen atom; $C_{2-8}$-alkoxyalkyl, $C_{1-4}$-alkoxyphenyl, $C_{1-4}$-alkoxy-benzyl, tetrahydrofuranyl, $C_{2-4}$-alkyl-piperidinyl, $C_{2-4}$-alkyl-morpholinyl or $C_{2-4}$-alkyl-piperazinyl, $R_2$ is a $C_{1-4}$-alkyl group, and $R_3$ is a $C_{1-6}$-alkyl group, comprising reacting racemic 4-aryl-2-oxo-pyrrolidine-3-carboxylic acid esters in aqueous phase with pancreatin or cholesterol esterase, to form an optically active 4-aryl-2-oxo-pyrrolidine- 3-carboxylic acid of formula II

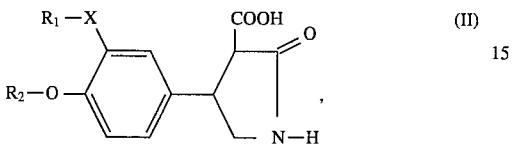

(II)

in which X, $R_1$ and $R_2$ have the above-named meaning and recovering one or more optical isomers thereof.

2. A process according to claim 1, wherein $R_1$ is $C_{1-8}$-alkyl, $C_{2-8}$-alkenyl, $C_{2-8}$-alkynyl, $C_{3-6}$-cycloalkyl, $C_{4-8}$-cycloalkylalkyl, phenyl, or benzyl.

3. A process according to claim 1, wherein X is an oxygen atom, $R_1$ is ethyl, isopropyl, 2-propinyl, cyclopropylmethyl, cyclopentyl or benzyl and $R_2$ is methyl.

4. A process for the resolution of racemates of 4-aryl-2-oxo-pyrrolidine- 3-carboxylic acid esters of the formula I

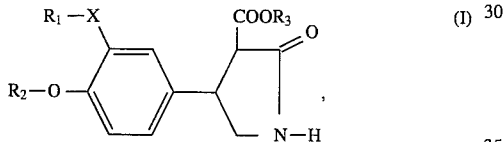

(I)

wherein

X is an oxygen atom and $R_1$ is

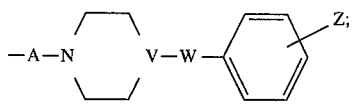

$R_2$ is a $C_{1-4}$-alkyl group, and $R_3$ is a $C_{1-6}$-alkyl group, comprising reacting racemic 4-aryl-2-oxo-pyrrolidine-3-carboxylic acid esters in aqueous phase with pancreatin or cholesterol esterase, to form an optically active 4-aryl-2-oxo-pyrrolidine- 3-carboxylic acid of formula II

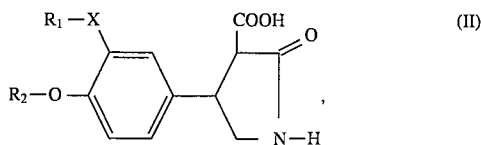

(II)

in which X, $R_1$ and $R_2$ have the above-named meaning and recovering one or more optical isomers thereof wherein A is $C_{2-4}$-alkylene substituted by hydroxy, V is N or a methine group, W is an N—C bond, a C—C bond, a methylene group or a carbonyl group, and Z is hydrogen or halogen.

5. A process according to claim 4, wherein $R_2$ is methyl.

6. In a process for the production of an (+)-enantiomer of an optically active 4-aryl-2-oxo-pyrrolidine of formula III

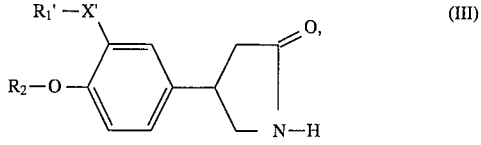

(III)

wherein

X' is a carbon-carbon bond or an oxygen atom, $R_1'$ is a $C_{1-16}$-hydrocarbon radical optionally substituted by at least one hydroxy group, and/or halogen atom; $C_{2-8}$-alkoxyalkyl, $C_{1-4}$-alkoxyphenyl, $C_{1-4}$-alkoxybenzyl, tetrahydrofuranyl, $C_{2-4}$-alkyl-piperidinyl, $C_{2-4}$-alkyl-morpholinyl or $C_{2-4}$-alkyl-piperazinyl, or $R_1'$—X' is a hydroxy group, and $R_2$ is a $C_{1-4}$-alkyl group, from a racemic mixture of 4-aryl-2-oxo-pyrrolidine-3-carboxylic acid esters of the formula

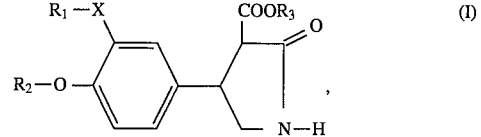

(I)

wherein $R_1$ is the same as $R'_1$, X is the same as X', and $R_3$ is a $C_{1-6}$-alkyl group, the improvement comprising reacting a racemic mixture of formula (I) with pancreatin or cholesterol esterase and separating said (+)-enantiomer of formula (III).

* * * * *